United States Patent

Cartmell et al.

Patent Number: 5,830,212
Date of Patent: Nov. 3, 1998

[54] ELECTROSURGICAL GENERATOR AND ELECTRODE

[75] Inventors: Robert Louis Cartmell, Dayton, Ohio; David Malcolm Tumey, San Antonio, Tex.

[73] Assignee: NDM, Inc., Utica, N.Y.

[21] Appl. No.: 735,205

[22] Filed: Oct. 21, 1996

[51] Int. Cl.$^6$ ................................................. A61B 17/39
[52] U.S. Cl. .............................. 606/35; 606/32; 128/908
[58] Field of Search ........................ 606/32, 35; 128/908

[56] References Cited

U.S. PATENT DOCUMENTS

| | | |
|---|---|---|
| 4,200,104 | 4/1980 | Harris . |
| 4,303,073 | 12/1981 | Archibald . |
| 4,416,276 | 11/1983 | Newton et al. . |
| 4,416,277 | 11/1983 | Newton et al. . |

FOREIGN PATENT DOCUMENTS 2516782  5/1983  France ..................................... 606/35

Primary Examiner—Lee S. Cohen
Attorney, Agent, or Firm—Killworth, Gottman, Hagan & Schaeff, LLP

[57] ABSTRACT

An electrosurgical generator has an active electrode output connector and a return current connector, the generator providing an electrosurgical current at the active electrode output connector, and including a fault detection circuit for monitoring the proper operation of the generator. An active electrode is connected to the active electrode output connector for receiving the electrosurgical current from the generator and applying the electrosurgical current to a patient. A patient return electrode provides capacitive coupling with the skin of a patient. A patient return electrode cable is electrically connected to the patient return electrode. An interface module is electrically connected to the return current connector of the generator and to the patient return electrode cable for permitting return of the electrosurgical current from the patient to the generator via the patient return electrode and the patient return electrode cable. The interface module electrically simulates to the fault detection circuit of the electrosurgical generator a fault condition when the patient return electrode does not provide sufficient contact with the skin of a patient, whereby operation of the electrosurgical generator is terminated.

17 Claims, 6 Drawing Sheets

ELECTROSURGICAL GENERATOR AND ELECTRODE

BACKGROUND OF THE INVENTION

The present invention relates to an electrosurgical generator apparatus and a capacitive patient return electrode and, more particularly, to an interface module that may be used with an electrosurgical generator to provide for discontinuance of the operation of the generator in the event that the patient return electrode is not sufficiently attached to a patient.

Electrosurgery has become quite common for a number of reasons. Controlling bleeding during surgery is a significant problem, and it has been found that coagulation, or hemostasis, can be accomplished by applying a radio frequency current to the affected patient tissue. Further, it has been found that applying a radio frequency current to tissue through a scalpel acting as the active electrode facilitates the cutting action of the scalpel. Typically, an electric current is applied to the tissue of a patient via the scalpel at the same time that the scalpel is used to cut the tissue in a conventional manner. It is known that certain current wave shapes and frequencies enhance the cutting action of the electrosurgical scalpel, while other current wave shapes and frequencies tend to cause coagulation of blood in the region of an incision.

The electric current for electrosurgical procedures is provided by a generator including a radio frequency oscillator circuit. The electrosurgical current is applied to the patient by the active electrode connected to the generator by a cable, and is returned from the patient to the generator through a cable which is attached to a patient return electrode, which is secured to the patient's skin. The patient return electrode is relatively large in area, thereby keeping the current density in the region of the patient return electrode sufficiently low to avoid tissue burns.

Prior art patient return electrodes have either been of the direct electrical contact type or of the capacitively coupled type. Direct electrical contact type patient return electrodes have either been designed to be attached directly to or placed underneath a patient and have been available in both dry (direct metal contact to skin) and conductive gel or adhesive (electrode coupled to skin through a conductive solution, gel, or polymer) forms. An example of one such electrode is disclosed in U.S. Pat. No. 4,722,761, issued Feb. 2, 1988, to Cartmell et al, and assigned to the assignee of the present invention. Capacitively coupled patient return electrodes typically have an electrically conductive layer covered with a layer of dielectric material. U.S. Pat. No. 4,669,468, issued Jun. 2, 1987, to Cartmell, assigned to the assignee of the present invention, discloses such an electrode.

It will be appreciated that if the patient return electrode should become partially detached from the patient, the density of the current in the region of the skin surface remaining in contact with the electrode would be significantly increased, perhaps to the point of injury to the patient. Further, a partially detached patient return electrode increases significantly the impedance of the return path to the return current connector of the electrosurgical generator. This increased impedance makes the possibility of significant current return to the generator through alternate ground paths. If such an alternate ground path is presented, it is common that the surface area of the grounded element in contact with the skin of the patient is relatively small, resulting in a large and potentially harmful current density.

Several different approaches have been taken to detect a fault in the proper operation of the generator, including its current return circuit, and to discontinue operation of the generator in response to the detection of the fault. As used herein, the word "fault" means any of various defects in the current return path, and not merely a "fault to ground."

One common approach has been to monitor the electrical continuity of a patient return electrode cable through means of a cable continuity circuit. The cable is a two conductor cable which is connected to a return current connector on the generator having a pair of conductors. A small electrical test signal which is applied to one of the cable conductors, travels down the cable conductor, through the electrode, and up the other cable conductor to the generator where it is sensed. If the test signal is not sensed, then operation of the generator is terminated. This verifies that the cable is attached to the generator and to a electrode, but does not provide an indication of whether the electrode is attached to a patient or the degree of attachment.

Another approach that has been taken to detect a fault in the proper operation of the generator is a return electrode monitor. Such a circuit, typically provided as a part of the generator, requires the use of a conductive electrode having a pair of electrically separated elements on the patient return electrode. The electrically separated elements on the patient return electrode are connected to respective ones of the pair of conductors in the patient return electrode cable. The return electrode monitor (sometimes referred to as "REM") checks periodically for an appropriate resistive coupling (skin resistance) between the return current connector conductors. If an inappropriate resistance is detected, the generator is disabled.

Previously, it has not been possible to operate with a capacitive patient return electrode with a generator having a REM circuit. Further, no simple means of utilizing generators having REM or cable continuity circuits with capacitive patient return electrodes has been available in which the attachment of the electrode is monitored.

SUMMARY OF THE INVENTION

These needs are met by apparatus constructed according to the present invention for performing electrosurgical procedures. The apparatus includes an electrosurgical generator having an active electrode output connector and a return current connector, the generator providing an electrosurgical current at the active electrode output connector, and including a fault detection circuit for monitoring the proper operation of the generator; an active electrode connected to the active electrode output connector for receiving the electrosurgical current from the generator and applying the electrosurgical current to a patient; a patient return electrode providing capacitive coupling with the skin of a patient; a patient return electrode cable, electrically connected to the patient return electrode; and an interface module electrically connected to the return current connector of the generator and to the patient return electrode cable for permitting return of the electrosurgical current from the patient to the generator via the patient return electrode and the patient return electrode cable. The interface module electrically simulates to the fault detection circuit of the electrosurgical generator a fault condition when the patient return electrode does not provide sufficient contact with the skin of a patient, whereby operation of the electrosurgical generator is terminated.

The fault detection circuit for monitoring the proper operation of the generator may be a return electrode monitor circuit. With this arrangement, the interface module electrically disconnects the return current connector of the generator from the patient return electrode cable when the patient return electrode does not provide sufficient contact with the skin of a patient, whereby operation of the electrosurgical generator is terminated.

The return current connector comprises a pair of connector conductors. The fault detection circuit for monitoring the proper operation of the generator may be a cable continuity monitor circuit which monitors the electrical continuity between the pair of connector conductors. With this arrangement, the interface module interrupts the electrical continuity between the pair of connector conductors when the patient return electrode does not provide sufficient surface area contact with the skin of a patient, whereby operation of the electrosurgical generator is terminated.

The patient return electrode includes a pair of patient return electrode elements, each providing capacitive coupling with the skin of a patient, and the patient return electrode cable includes a pair of cable conductors, each cable conductor electrically connected to an associated one of the patient return electrode elements. The pair of patient return electrode elements may each include an electrically conductive layer and an overlying dielectric layer. The electrically conductive layers are generally triangular in shape and not symmetrically positioned on the patient return electrode. More specifically, the electrically conductive layers are not symmetrically positioned with respect to a center line extending parallel to either the length or width of the patient return electrode.

In one embodiment, the interface module may comprise a fixed frequency oscillator circuit providing an oscillating output signal; a toroidal coil having a secondary winding connected to the output from the fixed frequency oscillator circuit and having a center-tapped primary winding with each end of the primary winding of the toroidal coil being connected to a respective one of the pair of cable conductors, the toroidal coil and the parallel connected capacitance provided by the pair of patient return electrode elements of the patient return electrode providing a tank circuit, whereby the resonant frequency of the tank circuit varies with the degree of attachment of the patient return electrode, and the current in the tank circuit is inversely related to the degree of attachment of the patient return electrode; a comparator circuit for comparing the current in the tank circuit to a reference level; and a switch circuit for electrically simulating to the fault detection circuit of the electrosurgical generator a fault condition when the current in the tank circuit exceeds the reference level, whereby operation of the electrosurgical generator is terminated when the patient return electrode does not provide sufficient surface area contact with the skin of a patient.

The interface module may further comprise a sample and hold circuit for sampling the current in the tank circuit at the time that the patient return electrode is initially applied to a patient so as to establish the reference level, with the sample and hold circuit providing the reference level to the comparator circuit. The interface module may also comprise a self-test circuit for actuating the switch circuit in the event of a component failure in the interface module. The interface module additionally comprises a window circuit for enabling operation of the comparator circuit only during periods of time in which the generator is not supplying the electrosurgical current to the active electrode.

In another embodiment, the interface module may comprise a variable frequency oscillator circuit providing an oscillating output signal, with the oscillator circuit including a manually adjustable frequency control; a toroidal coil having a secondary winding connected to the output from the variable frequency oscillator circuit, and having a center-tapped primary winding with each end of the primary winding of the toroidal coil being connected to a respective one of the pair of cable conductors, the toroidal coil and the parallel connected capacitance provided by the pair of patient return electrode elements of the patient return electrode providing a tank circuit, whereby the resonant frequency of the tank circuit varies with the degree of attachment of the patient return electrode, and the current in the tank circuit is inversely related to the degree of attachment of the patient return electrode; a comparator circuit for comparing the current in the tank circuit to a reference level; and a switch circuit for electrically simulating to the fault detection circuit of the electrosurgical generator a fault condition when the current in the tank circuit exceeds the reference level, whereby operation of the electrosurgical generator is terminated when the patient return electrode does not provide sufficient contact with the skin of a patient.

In another embodiment of the invention, the interface module may comprise a toroidal coil having a center-tapped primary winding with each end of the primary winding of the toroidal coil being connected to a respective one of the pair of cable conductors, the toroidal coil having a secondary winding in which a current is generated during generator activation that varies directly in magnitude with the degree of attachment of the patient return electrode, and the current in the tank circuit is inversely related to the degree of attachment of the patient return electrode; and a switch circuit for electrically simulating to the fault detection circuit of the electrosurgical generator a fault condition when the current in the secondary winding exceeds a predetermined level, whereby operation of the electrosurgical generator is terminated when the patient return electrode does not provide sufficient contact with the skin of a patient.

A generally rectangular patient return electrode according to the present invention for use with an electrosurgical generator may comprise a generally rectangular, electrically non-conductive support layer, a pair of patient return electrode elements mounted on the support layer, each element including an electrically conductive layer and an overlying dielectric layer, the electrically conductive layers being generally triangular in shape and each including a cable connection tab portion for engagement with a separate cable conductor of a patient return electrode cable, the electrically conductive layers being positioned asymmetrically with respect to the center line of the electrode extending parallel to either the length or width of the patient return electrode.

Accordingly, it is an object of the present invention to provide apparatus for performing electrosurgical procedures in which a capacitive patient return electrode is used and in which the degree of attachment of the patient return electrode is monitored; to provide such apparatus in which an interface module may be connected between the capacitive patient return electrode and the return current connector of the electrosurgical generator for simulating to the electrosurgical generator a fault condition which may be detected to discontinue operation of the generator; and to provide a split element patient return electrode for use with such apparatus.

Other objects and advantages of the invention will be apparent from the following detailed description, the accompanying drawings, and the appended claims.

DETAILED DESCRIPTION OF THE PREFERRED EMBODIMENTS

Figure 1:
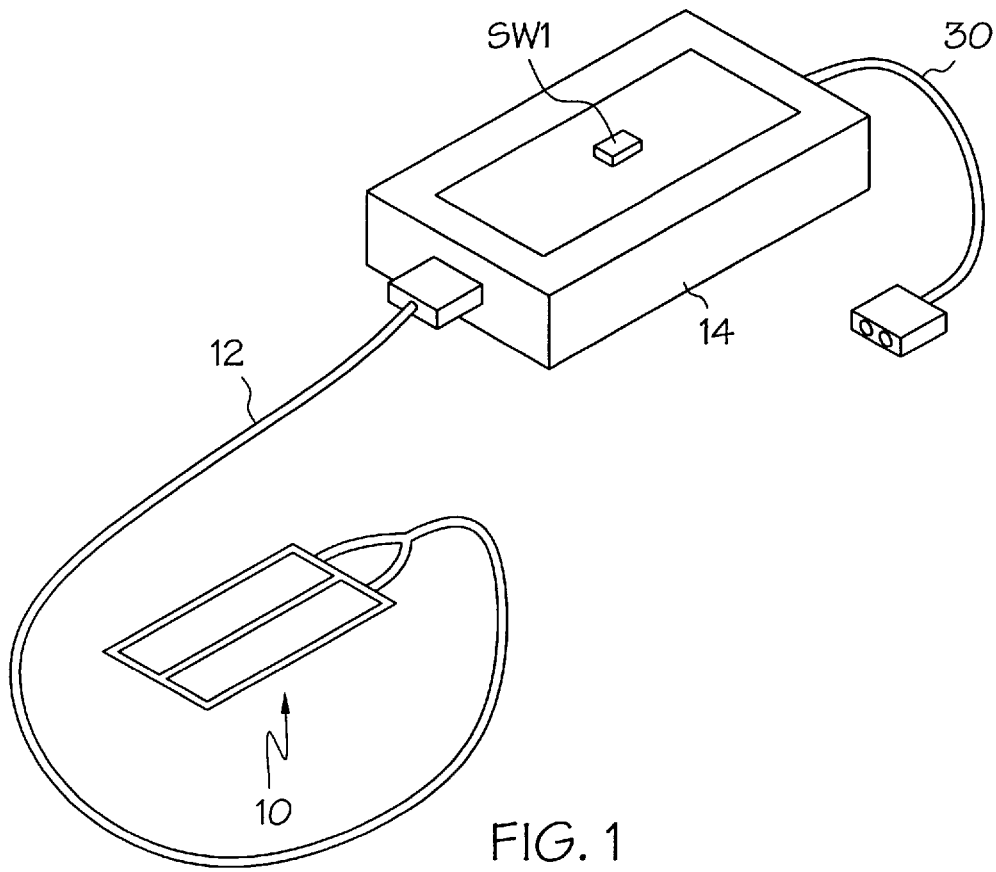
FIG. 1 illustrates an interface module and a patient return electrode and cable according to the present invention.
Figure 2:
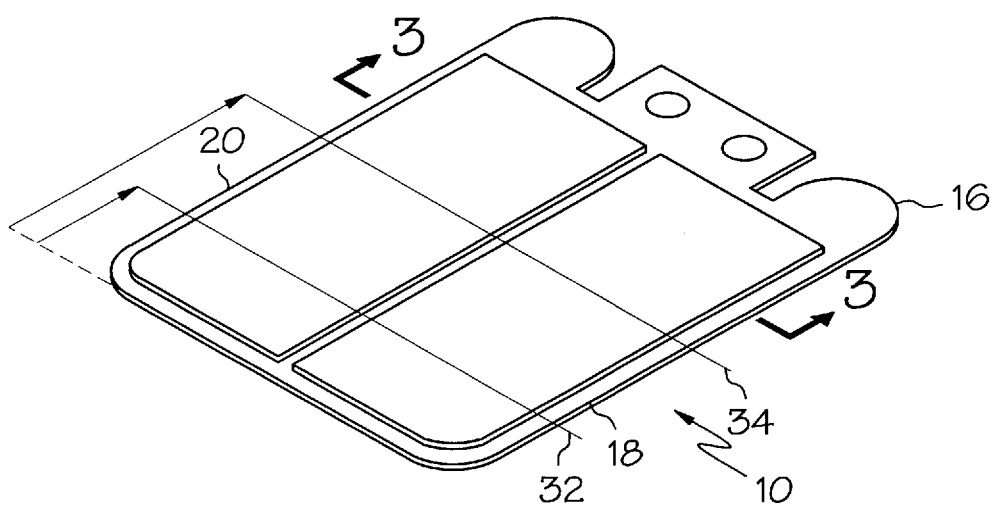
FIG. 2 is a perspective drawing showing a patient return electrode having a pair of electrical elements.
Figure 3:
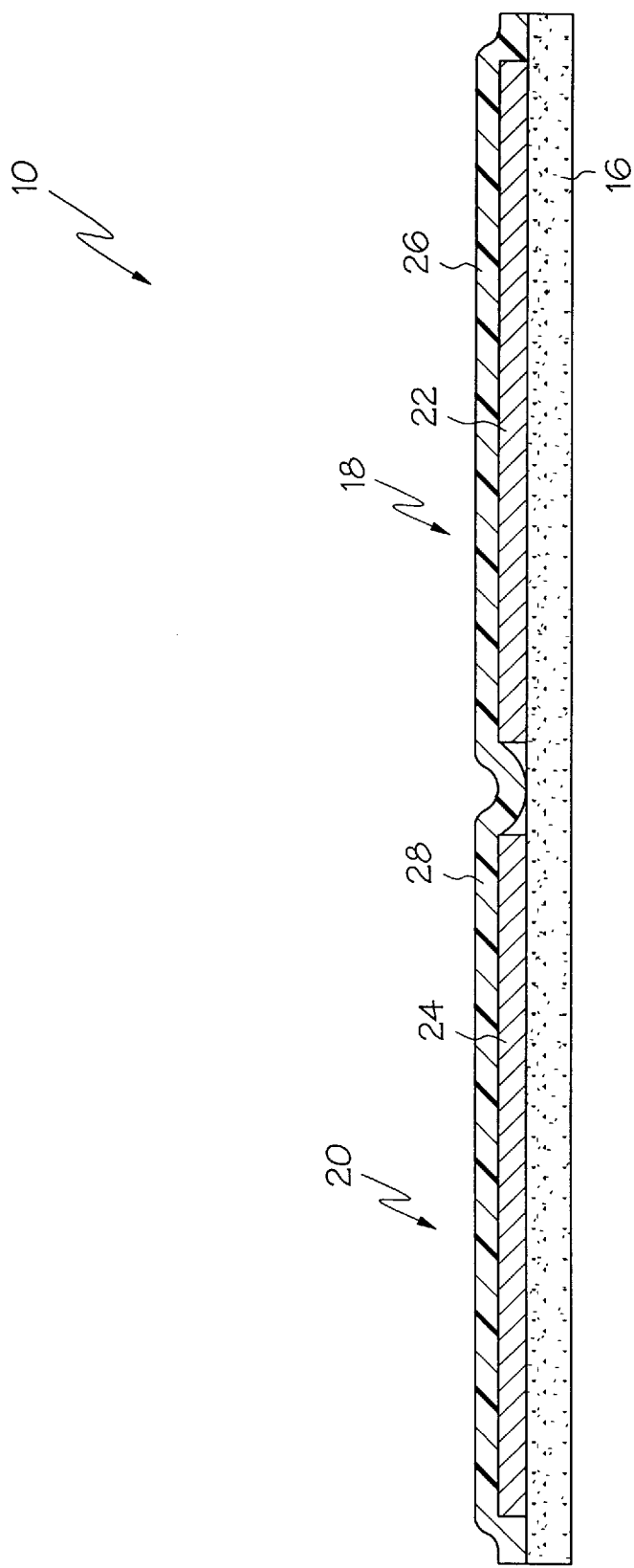
FIG. 3 is a sectional view of the electrode of FIG. 2, taken generally along line 3—3 in FIG. 2.

Reference is made to FIGS. 1–4 which illustrate apparatus for performing electrosurgical procedures according to a first embodiment of the present invention. The apparatus includes an electrosurgical generator having an active electrode output connector and a return current connector (not shown) The generator provides an electrosurgical current at the active electrode output connector. The generator includes a fault detection circuit for monitoring the proper operation of said generator. The fault detection circuit may be either a cable continuity monitor circuit or a return electrode monitor circuit. An active electrode (not shown) is connected to the active electrode output connector for receiving said electrosurgical current from said generator and applying said electrosurgical current to a patient.

A patient return electrode 10 provides capacitive coupling with the skin of a patient. A patient return electrode cable 12 is electrically connected to the patient return electrode 10. An interface module 14 is electrically connected to the return current connector of the generator and to the patient return electrode cable 12 for permitting return of the electrosurgical current from the patient to the generator via the patient return electrode 10 and the patient return electrode cable 12. In a manner described below, the interface module 14 electrically simulates a fault condition to the fault detection circuit of the electrosurgical generator when the patient return electrode 10 does not provide sufficient contact with the skin of a patient. The fault detection circuit then terminates operation of the electrosurgical generator.

The patient return electrode 10 is generally rectangular, and includes a generally rectangular, electrically non-conductive support layer 16 which may comprise a foam layer. A pair of patient return electrode elements 18 and 20 are mounted on the support layer 16, preferably by means of adhesive. Elements 18 and 20 each include an electrically conductive layer 22 and 24, respectively. Elements 18 and 20 further include overlying dielectric layers 26 and 28.

The interface module 14 is used in the following manner. First, a capacitive patient return electrode 10 is applied to the patient in an appropriate location outside the surgical field. Next, the two wire cable 12 that is connected to the two elements 18 and 20 is attached the interface module 14. The module 14, in turn, is then connected to the electrosurgical generator's return current connector. For generators with an existing return electrode monitor or cable sentry, the interface module presents a simulation to the REM that the generator is connected to a common type of conductive pad, i.e. a pad that has a direct current resistive connection to the patient.

Next, the interface module 14 is initialized or "baselined" to the individual patient. This action is necessary because of the small variance in capacitive coupling between the patient and the electrode across the patient population. Nominally, the electrode provides approximately 900 pf of capacitance when it is fully attached to the patient. Without initialization, the slight error introduced by the variance in coupling between patients could cause the interface module 14 to indicate a fault when none is present, or to allow the generator to operate when the electrode has become significantly detached. By incorporating a technique whereby the coupling differences between patients are compensated for prior to commencement of electrosurgery, the interface module 14 can provide a high level of protection for the patient, and operate at a higher level of reliability.

During the electrosurgical procedure, the interface module 14 monitors the status of the capacitive coupling between the electrode 10 and the patient. When the capacitance value shifts by approximately 300 pf (which equates to loosing about ⅓ of the pad attachment), the module 14 will provide a fault signal to the electrosurgical generator to which it is attached through cable 30. The generator is then "fooled" into thinking that it has lost resistive coupling to the patient and the REM causes it to cease operation. Since the interface module 14 must also pass the radio frequency return ground currents, a window feature allows module 14 to check the status of the electrode 10 only during the interval when the surgical generator is off. Since the surgical procedures utilize only intermittent operation of the electrosurgical scalpel, there is ample time to check the status of the electrode 10 to afford protection for the patient.

If the interface module 14 detects a fault during the surgical procedure, the electrode 10, which is assumed to be compromised, can be re-seated against the patient, or replaced at the discretion of the operating room personnel. After the electrode condition is corrected, the interface module 14 is "re-baselined" and the operation can continue.

When the procedure has been completed, the surgical generator is disabled and disconnected from the interface module 14. The module 14 is disconnected from the cable 12, and the electrode is removed from the patient.

The interface module 14 is essentially a very sensitive capacitance measurement circuit that is utilized to monitor the connection between an electrode and the patient undergoing the electrosurgery. The system must be able to detect when the capacitive coupling between the electrode and patient has decreased to a point that will cause injury to the patient's tissue due to heating effects produced by radio frequency energy ground currents. In addition to measuring the electrode-to-patient coupling, the interface module 14 also feeds these radio frequency return currents through to the electrosurgical generator. The module operates in a way that is transparent to the generator and it simulates for the generator a direct current resistive connection between the electrode and patient as is normally present with the conductive type return electrodes. To meet both of the above requirements, the system employs a toroidal inductor T1 that is arranged in such a way as to form a resonant circuit with the electrode-to-patient capacitance. The approximate resonant frequency of this tuned circuit is 230 KHz. The radio frequency return currents (which are at a lower frequency and out of the range of the tuned circuit) are fed from the electrode to the center tap of the toroidal inductor back to the generator. When the generator is in use, large radio frequency currents are present in the inductor and these spurious currents could cause the system to indicate incorrectly that a fault has occurred. To prevent this from happening, a separate circuit "gates" out the measurement portion of the interface module 14 when radio frequency energy from the generator is present in the toroidal coil. This gating or window action also prevents the interface module 14 from detecting any faults during the interval that the generator is active. As soon as the generator deactivates, the window is again opened and the circuit immediately checks the capacitance coupling for any changes. The duty cycle between activity and non-activity of the generator will normally provide ample "look-through" for the system.

Figure 4:
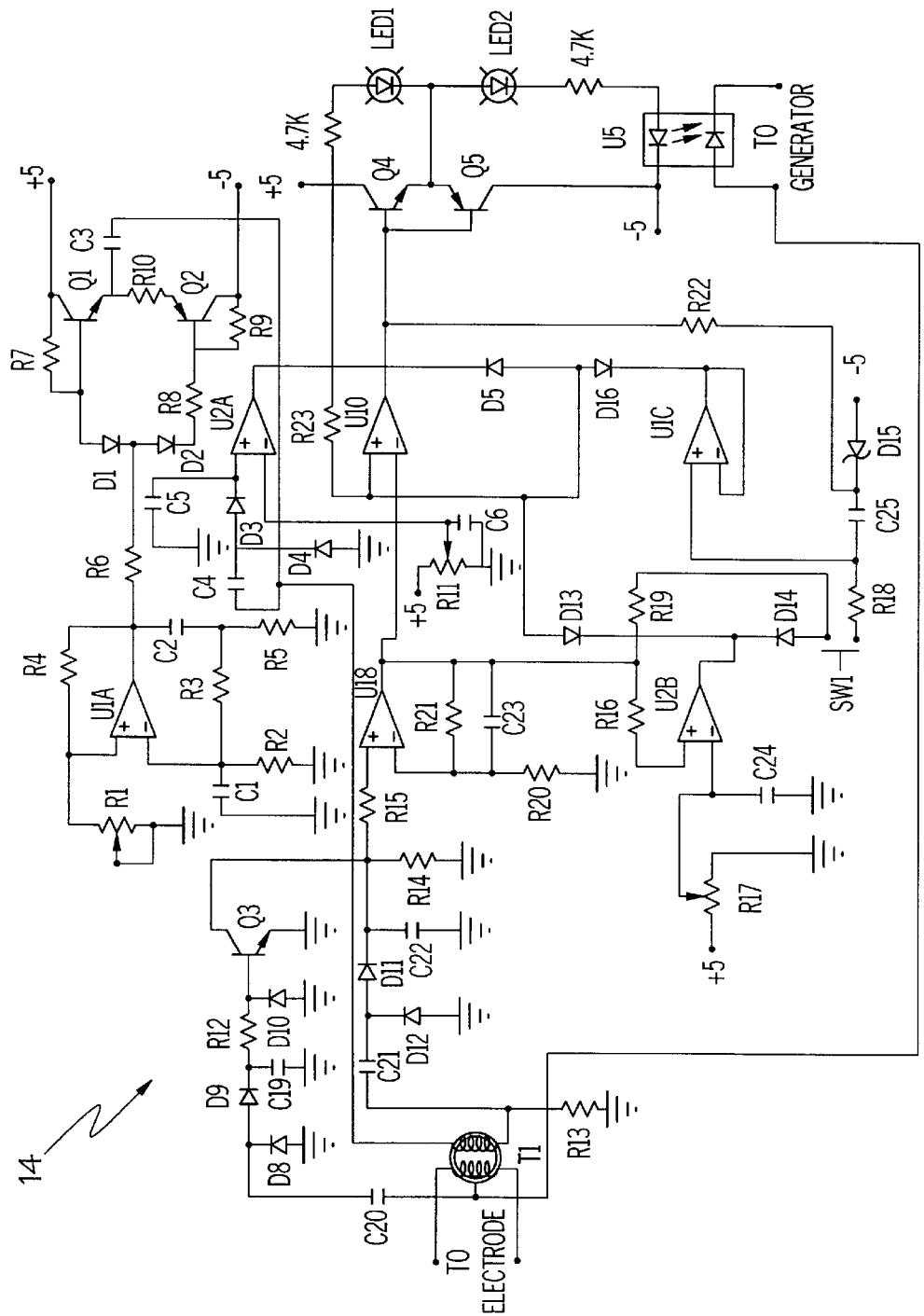
FIG. 4 is an electrical schematic diagram, illustrating the circuit of an interface module constructed according to a first embodiment of the present invention.

In the embodiment of FIG. 4, which utilizes a fixed sinusoidal oscillator, the tuned circuit formed by the toroidal inductor and the capacitance of the electrode-to-patient connection has a 230 KHz natural resonant frequency. The oscillator is fixed at a frequency (210 KHz) that is below the average resonant frequency for the largest part of the patient population. When the electrode is lifted, the capacitance between the electrode and patient decreases, and this has the effect of raising the natural resonant frequency of the tuned circuit. Since the resonant frequency is increasing, and the forcing signal provided by the fixed oscillator does not change, the forcing signal increasingly moves out of resonance with the tuned circuit. This causes additional current to flow in the tuned circuit which can be converted to a measurable electrical signal by the detection portion of the interface module. The detector provides an output voltage signal that varies in proportion to the amount of capacitance that is present between the electrode and patient. This signal is further amplified by addition circuitry for use with the fault circuits.

Initially, when the electrode is first connected to the patient, some unknown level of signal is present at the detector amplifiers. In order to measure the change in signal and hence the change in the electrode condition, a small sample of the signal is stored in a sample and hold circuit to enable a continuous comparison to take place between the original "baseline" condition of the electrode, and the changes that take place as the surgery proceeds. By pressing a button SW1 on the interface module 14, the system samples and stores this baseline signal level. As long as the signal level continuously measured by the interface module 14 stays below a preset fault threshold, the system will not indicate a fault, and will allow the generator to operate properly by providing a resistive connection between its ground return terminals.

When the electrode is lifted from the patient, and the capacitance between the electrode and patient is decreased by approximately ⅓ (indicated at 32 in FIG. 2, assuming that the electrode was lifted from the patient at the left edge), the signal level as detected and amplified by the circuits as described above will exceed a threshold difference (between the stored value and the continuously measured value) which triggers a comparator circuit that causes a fault signal to be produced. The fault signal lights a red LED1 and deactivates an electronic switch that normally provides a resistive connection between the pair of connector conductors in the return current connector of the generator. When the generator loses this resistive connection, fault detection circuit disables the internal circuitry that is otherwise necessary for radio frequency activation. The unit remains in the fault mode, until the electrode is corrected and the interface module is reinitialized by storing a new baseline value in memory.

In addition to the electrode fault detection circuitry, the interface module incorporates self-test circuits designed to enhance further the safety provided to the patient in the event of a system failure. If the power were to fail or be interrupted during a surgical procedure, the interface module would trigger a fault and remain in fault mode until reinitialized. If the oscillator circuit that provides the necessary forcing signal to the toroidal tuned circuit were to fail or be shorted to ground in some way, a detection circuit would trigger a fault. If the electrode were to be removed past the ½ way mark 34, or if the electrode were to be incorrectly placed on the patient when first applied, a detection circuit does not allow the unit to be initialized.

The first embodiment of the invention includes an interface module, the circuitry for which is illustrated diagrammatically in FIG. 4. The circuit includes toroidal inductor T1 which, in combination with the coupling capacitance between the electrode 10 and the patient, forms a tank circuit having a natural resonant frequency of approximately 230 KHz with a nominal coupling capacitance of 900 pf. The toroidal coil T1 is driven by an oscillator circuit that forces the tank circuit at 210 KHz, slightly less than the natural resonant frequency of the tank circuit. The oscillator is of a Wein Bridge design and is formed by components U1A, R1, R2, R3, R4, R5, C1 and C2. The frequency of operation is determined by C1, C2, R3, R2 and adjustable resistor R1. R1 can be adjusted to provide exactly 210 KHz and is used to compensate for tolerance errors of the other timing components. The output from the oscillator is coupled to the buffer amplifier via R6. Q1 and Q2 form a push-pull buffer amplifier circuit that provides about 0.5 Volts peak-to-peak through capacitor C3 to the toroidal inductor circuit. Capacitor C4, and diodes D3 and D4 form a detection circuit that monitors the output of the oscillator and the buffer amplifier. Should the oscillator and its related components fail, a fault signal would be sent to the electrosurgical generator. Integrated circuit U2A is utilized as a voltage comparator that triggers when the oscillator-fail detection envelope falls below a preset level determined by resistor R11.

When the electrode 10 is removed from the patient, the amount of coupling capacitance decreases, causing the natural frequency of the T1 tank circuit to increase. This increase in resonant frequency causes a corresponding increase in the tank circuits currents which are converted to a voltage signal by resistor R13. The output obtained as a voltage across R13 is detected by C21, D11, D12, C22 and R14. This output is applied to amplifier U1B through resistor R15 which is present to prevent oscillations. Amplifier U1B is configured as a non-inverting voltage amplifier with an approximate gain of 5.

The output of amplifier U1B is fed to comparator U2B through R16 where it is compared with a level set by resistor R17. U2B is utilized as a monitor that will trigger a fault when the electrode is removed to approximately the ½ way point (450 pf). In addition, the output of amplifier U1B is fed to U1C which is configured as a sample and hold circuit that is activated by depressing switch SW1. When the unit is first turned on and the electrode is connected to the patient, SW1 is depressed causing the baseline value of the electrode's capacitance be stored and maintained by capacitor C25, diode D15 and resistor R22. This stored value is maintained by these circuit elements until a fault is detected. Upon detection of a fault, R22 and Zener diode D15, reduce the sample value in such a way as to prevent the fault detection from clearing until the unit is re-initialized after the problem with the electrode has been corrected.

Integrated circuit U1D acts as a comparator and monitors the difference between the continuous signal from the detector amplifier and the stored value maintained by the sample-and-hold circuit. Should the electrode attachment be decreased by approximately one-third its initial value, U1D would trigger causing the electrosurgical generator to shut down. The difference threshold is set by the voltage drop across diode D16 which connects the output of the sample-and-hold circuit to the input of U1D. The input of U1D is always 0.7 volts less than the actual sampled value. Diodes D13, D14 and D5 form an OR gate which connects the various self-test circuits to the fault detection comparator U1D.

The output of U1D is buffered by transistors Q4 and Q5 which provide the current necessary to drive diodes LED1 and LED2. LED1 is a red LED that is lit when a fault exists with the electrode. LED2 is a green LED that lights when the system has been baselined by depressing SW1. When the power has been removed from the circuit, capacitor C25 of the sample-and-hold circuit discharges through diode D15. Upon power-up, the red LED1 is lit until the system is baselined. Component U5 is an optically coupled triac switch device that provides the necessary D.C. resistive coupling needed to "fool" the electrosurgical generator into thinking that it is connected to the proper ground return electrode. When LED2 is active, the integrated LED inside U5 causes the IC to conduct and make connection to the electrosurgical generator. As soon as a fault is detected by U1D, LED2 is extinguished, red LED1 is lit, and U5 deactivates causing the generator to become disabled. This circuit is responsible for providing the REM fault to the electrosurgical generator.

When the generator is activated and is producing large levels of radio frequency energy, inductor T1 experiences increased current levels which cause large spikes in the output signal obtained via the detection circuits. In order to prevent the system from detecting a false fault condition during these intervals, it is necessary to provide a "look-through" window circuit that shuts the detection circuits off when the generator is active. This circuit is comprised of C20, D8, D9, C19, R12, D10 and transistor Q3. Q3 is configured in such a way as to clamp the detector signal present across resistor R14 prior to amplification by U1B. A small sample of the radio frequency energy returning through the ground circuit is coupled via C20 to a diode detection circuit made up of D8 and D9. This signal provides forward bias to transistor Q3 through resistor R12. When the transistor is forward biased, it is on and the window is closed. Diode D10 is designed to protect the transistor from large reverse bias voltages that could otherwise damage its base-emitter junction.

Figure 5:
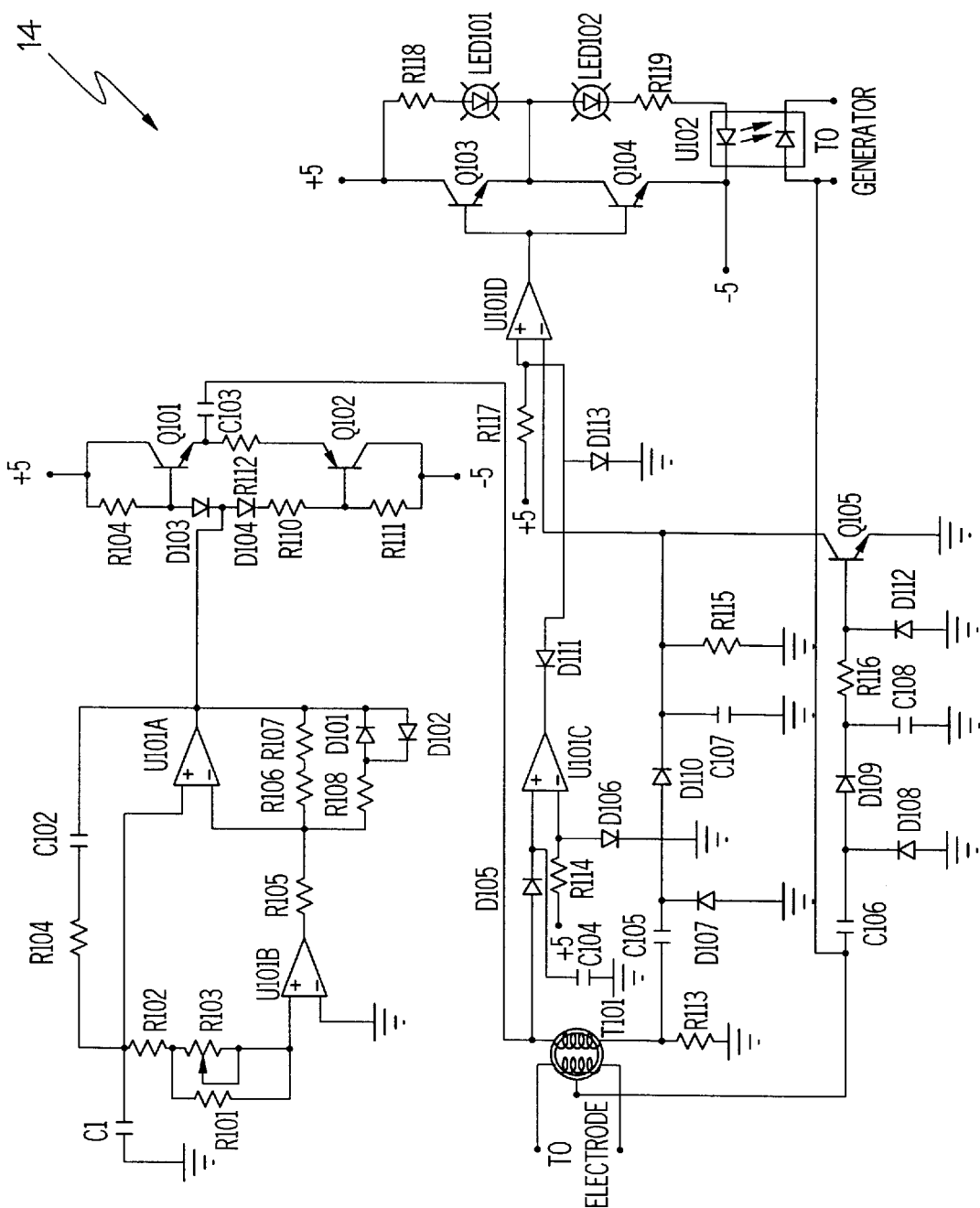
FIG. 5 is an electrical schematic diagram, illustrating the circuit of an interface module constructed according to a second embodiment of the present invention.

Reference is now made to FIG. 5 which illustrates a second embodiment of the interface module of the present invention. This interface module utilizes much of the same circuitry as described above with respect to the first embodiment, except that instead of utilizing a fixed frequency sinusoidal generator, the frequency can be varied by a sliding resistor. The range of the generator is 185 KHz to 260 KHz, which brackets the natural resonant frequency of approximately 230 KHz. This allows the device to be tuned to the exact resonant frequency of the tuned circuit regardless of the coupling capacitance variations. When the electrode is first connected to the patient, the wiper on the sliding resistor is moved causing the oscillator (that is forcing the tuned circuit) to move into resonance with the tuned circuit. At this point, a current having the minimum amplitude flows in this circuit. This current, as described above with respect to the first embodiment, is converted by a detection circuit into a voltage signal amplitude that is representative of the amount of current flowing in the tuned circuit. When the electrode is lifted as described before, the tuned circuit tends to move out of resonance with the forcing signal applied by the sinusoidal oscillator. This has the effect of increasing the signal output level from the detection circuit element, which triggers a preset threshold and causes a fault signal to occur.

The advantage of this approach is that no sample need be taken of the detector output signal as a baseline. This eliminates any possibility of drift error that might occur over time, or if the devices were subjected to large shifts in ambient temperature. By selecting an oscillator frequency that is perfectly resonant with the tuned circuit, all error caused by variation from patient to patient is effectively canceled. Only the difference in coupling capacitance is measured once the resonant frequency changes due to changing electrode connectivity are eliminated. An additional advantage of this embodiment is that it utilizes fewer components than the first embodiment.

As with the first embodiment, the central portion of the embodiment of FIG. 5 consists of the tuned circuit that is composed of toroidal inductor T101 and the coupling capacitance between the electrode 10 and the patient. The tank circuit has a natural resonant frequency of approximately 230 KHz (assuming a coupling capacitance of 900 pf). As with the first embodiment, the toroidal coil T101 is driven by an oscillator circuit that forces the tank circuit at a desired frequency. The principal difference between the two embodiments is that the first embodiment utilizes a fixed frequency oscillator, while the second embodiment uses a variable frequency oscillator.

The oscillator in the second embodiment can be adjusted by the user during the initialization step to match the natural resonant frequency of the tank circuit. In this way, small variations due to the different coupling capacitances derived across the population of patients can be canceled by adjusting the frequency of the forcing oscillator. The oscillator also must maintain a nearly constant amplitude across its tuning range which nominally is between 185 KHz and 260 KHz. The circuit employed to perform this function is of a modified Wein Bridge design that incorporates two operational amplifiers instead of the single amplifier design of the first embodiment. By using the second amplifier to provide control of the loop gain, an easily tuned oscillator can be realized. The tuning requires adjustment of a single resistor whereas with a standard unmodified Wein Bridge oscillator, tuning requires the adjustment of two resistors which must track each other very accurately.

The oscillator circuit is formed by U101A, U101B, R101, R102, R103, R104, R105, R106, R107, R108, capacitors C101 and C102, and diodes D101 and D102. The time constants for the oscillator are set by capacitors C101 and C102 and resistors R101, R102, R103 and R104. R103 is an adjustable potentiometer that varies the frequency across the tuning range. Diodes D101, D102 and resistor R108 are utilized to maintain a constant amplitude output signal. Resistors R105, R106, R107 and amplifier U101A provide the necessary feedback gain to maintain proper oscillation. Transistors Q101 and Q102 form a push-pull amplifier circuit that buffers the oscillator and provides approximately 1.5 volts peak-to-peak to the toroidal inductor through coupling capacitor C103.

When the electrode 10 is lifted from the patient, the amount of coupling capacitance decreases causing the natural frequency of the T101 tank circuit to increase. This increase in resonant frequency causes a corresponding increase in the tank circuit currents which are converted to a voltage signal by resistor R113. This technique for detection is identical with the methods employed in the first embodiment. The output signal obtained as a voltage developed across R113 is detected by C105, D107, D110, C107 and R115. This output signal is applied to the non-inverting input of U101D which is configured as a comparator with the threshold voltage determined by resistor R117 and diode D113. When the electrode is lifted and the output signal increases past the threshold, U1D produces a fault signal that is sent to disable the electrosurgical generator. When the electrode is lifted beyond the half-way point, the resonant frequency of the tank circuit increases to a point beyond which the oscillator circuit can be tuned. This feature makes it impossible for the system to be properly initialized when the electrode is not correctly attached to the patient when it is first applied.

During the intervals where the electrosurgical generator is active and producing radio frequency energy, the currents through the tank circuit increase to levels that would be indicative of a fault. To prevent the system from falsing during these periods, a window or gate circuit similar to the one employed in the first embodiment is utilized. A sample of radio frequency energy from the ground return is fed to the window circuit through capacitor C106. This signal is rectified and detected by diodes D108 and D109 and filtered by capacitor C108. The current is then used to forward bias transistor Q105, turning it on. When transistor Q105 is switched on, the signal applied to the non-inverting input of U101D is shunted to ground, preventing any detected electrosurgical energy from triggering the comparator and causing a false alarm. As soon as the electrosurgical generator is deactivated, Q105 is no longer forward biased and ceases to conduct. When Q105 shuts off, the signal is restored to U101D and the system can resume monitoring the condition of the capacitive electrode.

Should the oscillator circuit fail or should the conductive plates within the electrode become shorted, the self-test circuit comprised of D105, C104, R114, D106 and U101C will cause a fault signal to be generated by forward biasing diode D111 and reducing the trigger threshold of U101D.

As with the first embodiment, the output of fault detection circuit U101D is buffered by transistors Q103 and Q104 which provide the current necessary to drive diodes LED101 and LED102. LED101 is a red LED that is lit when a fault exists with the electrode. LED102 is a green LED that illuminates when the system has been initialized by adjusting R103 for resonance after the electrode has been applied to the patient. When the power has been removed or should the power fail, LED101 will light momentarily and a fault signal will be sent to the electrosurgical generator. Component U102 is an optically coupled triac-like device that provides the necessary D.C. resistive coupling required to simulate for the electrosurgical generator the connection to a proper ground return electrode. When green LED102 is active, the integrated LED inside U102 causes the IC to conduct and make connection to the electrosurgical generator. As soon as a fault is detected by U101D, LED102 is extinguished, red LED101 is lit and U102 deactivates causing the generator to become disabled.

Figure 6:
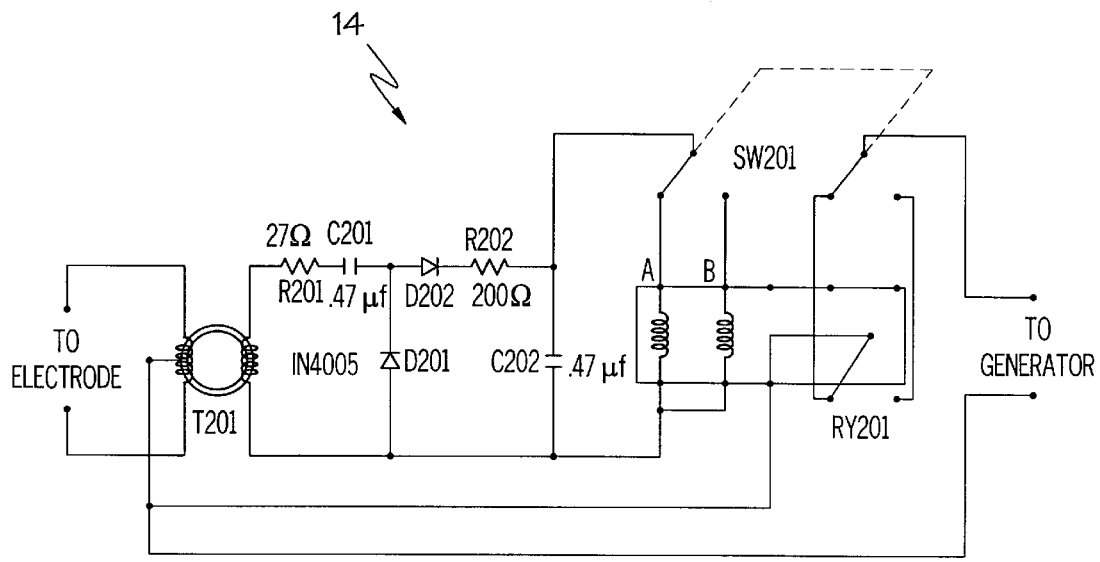
FIG. 6 is an electrical schematic diagram, illustrating the circuit of an interface module constructed according to a third embodiment of the present invention.
Figure 7:
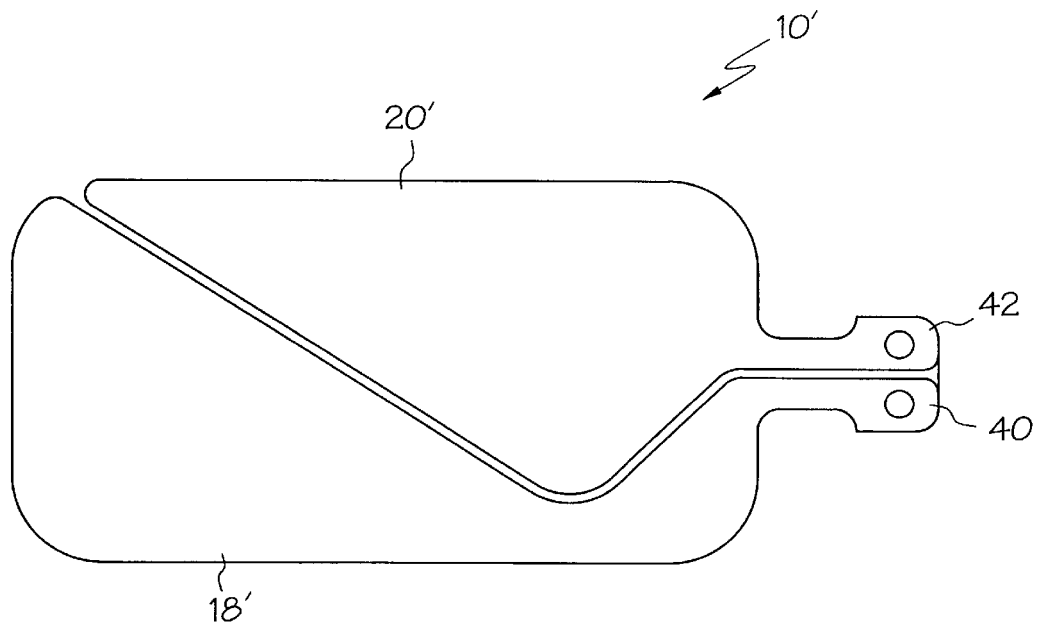
FIG. 7 illustrates the electrically conductive elements of a patient return electrode useful in operating with the interface modules shown in FIGS. 6 and 8.

Reference is now made to FIG. 6 which discloses a third embodiment of the interface module circuit. The third embodiment incorporates a patient return electrode 10', the shape and arrangement of the conductive elements of which are illustrated in FIG. 7. Other than the shape and orientation of the conductive elements 18' and 20', the electrode 10' is constructed identically with the electrode illustrated in FIGS. 2 and 3. The third embodiment of the interface module shown in FIG. 6 approaches the problem of detecting accidental disengagement of the grounding electrode differently than the previously described interface modules. Unlike the previously described embodiments, the third embodiment of the interface module requires a capacitive patient return electrode that has conductive elements split diagonally from one corner to the other, each half being identical in surface area. The interface module of FIG. 6 has many fewer components than the first two embodiments, and does not require an independent power source. Further, this interface module operates only during periods in which the generator is being operated. The electrically conductive elements 18' and 20' are generally triangular in shape, and each includes a cable connection tab portion 40 and 42, for engagement with a separate cable conductor of a patient return electrode cable. As will be noted, the electrically conductive elements are positioned asymmetrically with respect to the center line of the electrode extending parallel to either the length or width of the patient return electrode. It will be appreciated, therefore, that any partial removal of the electrode from the skin of the patient, assuming that it progresses from one end to the other or from one side to the other, will result in differing areas of the elements 18' and 20' being in contact with the skin of the patient.

The electrode of FIG. 7 combined with the interface module of FIG. 6 results in a current sensing arrangement that detects electrode disengagement. Imbalance of the return current occurs because of the non-symmetrical characteristics of the diagonal split grounding electrode. The interface module detects this current imbalance through a wound toroidal coil. When disengagement occurs, the toroidal coil generates a current that actuates a latching relay. The interface module then disables the electrosurgical generator, requiring the operator to reattach the electrode properly and to reset the interface module. Because the electrode and interface module use no external power, the trip point or amount of electrode disengagement that causes the interface module to shut down the surgical generator is function of the surface area removed for a given power setting. This system detects lift off with settings as low as 10 watts. The system ideally tracks the power and percentage of electrode lift off to shut down of the generator. Only a small percentage of electrode removal is required to shut down the generator at high power settings. When the power setting is low the condition for burns decreases and the system allows more of the electrode to be removed before the generator is shut down.

In order for the system of FIG. 6 to operate properly, the primary windings of the coil T201 should be accurately balanced. The return currents during activation of the surgical generator are in exact balance when the split electrode is fully attached to the patient. Therefore no voltage is developed in the secondary of T201. When the capacitive electrode starts to lift off the patient, the element 18' and 20' with the greater surface area remaining in contact creates a larger current in that half of the primary windings of T201. The voltage developed in the secondary of coil T201 is rectified and filtered with components R201, C201, D201, D202, R202, and C202. The value of R202 is chosen to compensate for the different energy and frequency characteristic of the two wave forms CUT and COAG employed by the electrosurgical generator. This value is chosen to balance the trip point of the electrode. For example at 50% power the system will shut down the generator at nearly the same percentage of electrode removal for both CUT and COAG.

The interface module of FIG. 6 includes a latching relay RY201, preferably relay model G6AK-234P, available from OMRON. However, other manufacturers' components with similar specifications are available. This component has critical electrical specifications and a unique magnetically biased coil that allows the relay to alternate contact closure with successive pulses of current. Once the relay has changed state it cannot be returned to the previous state without energizing the opposite coil. One set of relay contacts and one set of switch contacts is in series to short the patient monitoring system of the electrosurgical generator. In the event RY201 is actuated, SW201 must be repositioned to enable the generator. The SW201 contacts must always be in synchronous with the RY201 contacts short across the patient monitor of the generator. Switch SW201 is always set before use of the surgical generator to enable it.

Figure 8:
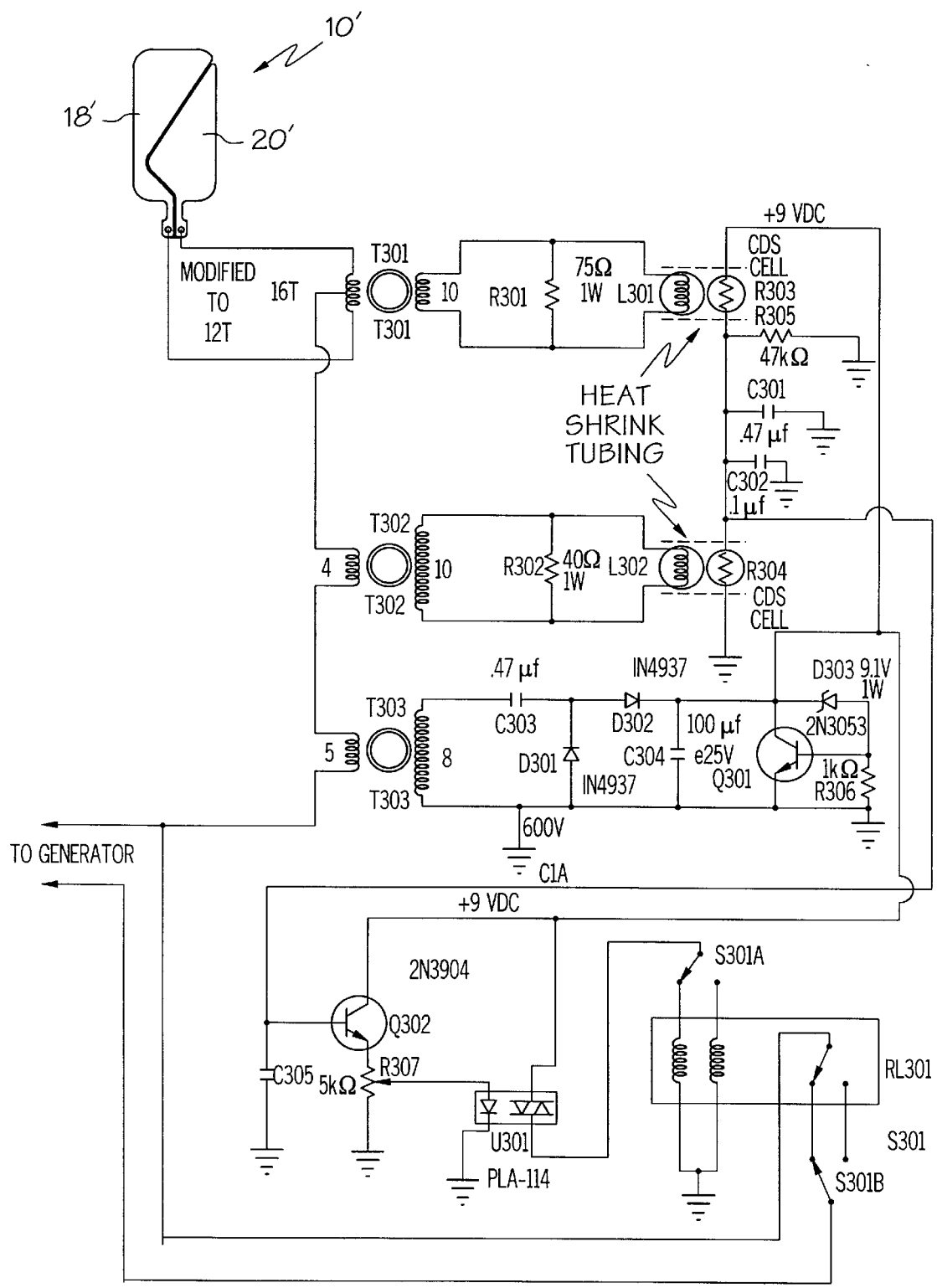
FIG. 8 is an electrical schematic diagram, illustrating the circuit of an interface module constructed according to a fourth embodiment of the present invention.

The fourth embodiment of the interface module is illustrated in FIG. 8, and incorporates two features not found in the third embodiment. The third embodiment only measured the differential current flow through each half of the electrode and did not have the ability to measure the total current flow. Thus, if the power of the electrosurgical generator was increased, the sensitivity of the system increased and would alarm with a smaller amount of electrode removed. Alternatively, if the power of the electrosurgical generator was decreased, the sensitivity would decrease and a greater portion of the electrode would need to be removed to trigger the alarm.

The embodiment of FIG. 8 eliminates this fluctuation in sensitivity. This embodiment also incorporates a clamp regulated D.C. power supply that makes use of the RF current from the generator to provide a constant 9 volt D.C. to power the detection circuits.

Three toroidal coils are utilized in the circuit. They are labeled T301, T302 and T303. T301 is nearly identical to the transformer used in the third embodiment of the interface module in that it provides an output which is proportional to the differential current flowing in each half of the primary. If the currents from each half of the electrode 10' are identical, the magnetic fields cancel in the primary of T301 and therefore, no output is delivered at the secondary. If however, the current flow is differential due to one plate area being smaller than the other (because of lift off), a current will flow in the secondary of T301. The primary winding of transformer T302 is in series with the center-tap of T301, and therefore the total current flowing in the ground return circuit flows through the primary of T302. Thus, a measure of the total current flow, and hence generator power level, is available at the secondary of T302. This signal can then be used to offset the differential current signal provided by T301. Transformer T303 is also in series with T302, and it provides, after proper rectification, filtering and regulation, a 9 volt D.C. power supply, with an available current of 200 MA.

The secondary of transformer T303 produces a current that varies with respect to generator power. The windings provide enough current to maintain an output of 9 volts D.C. even at the lowest power settings of the generator. Capacitor C303 couples the RF current from T303 to the rectifiers D301 and D302. The rectified D.C. voltage is stored across capacitor C304. If the voltage is below 9.1 volts, diode D303 acts as an open circuit, and therefore transistor Q301 is biased off, and no current flows between its collector and emitter which are also directly across C304. When the voltage across C304 (which is also impressed across D303 through resistor R306) exceeds 9.1 volts D.C., the diode begins to conduct, and current flows through the base-emitter junction of Q301 providing forward bias. Q301 then begins to conduct current and thus it provides a clamping action on the voltage that is allowed to develop across C304. This type of clamping regulation was found to be the most efficient and stable technique for providing a constant voltage level to the remaining circuits.

A power-tracking circuit is comprised of T302, R302 and L302. T302 provides a current that is directly proportional to the total current flow through the ground return circuit. The secondary of T302 is loaded by resistor R302, which provides a constant resistive load regardless of current flow. In addition, an incandescent lamp L302 is placed across R302 and the secondary of T302. This lamp will glow as current from T302 flows through it. The greater the amount of current flow, the brighter L302 will glow. Thus, the power being utilized by the generator can be measured by examining and quantifying the brightness of lamp L302. This is accomplished by resistor R304 which is a CDS cell having a resistance that is related to the amount of light striking its front surface. Resistor R304 and lamp L302 are assembled together in a light-tight enclosure preventing any stray light from striking R4 and affecting the measurements. If L302 is off, the resistance of R304 is extremely high, and as L302 increases in brightness, the resistance decreases rapidly at first, and then more slowly as the brightness reaches maximum. The inherent nonlinearity of CDS cell R304 is advantageous as it provides some additional sensitivity at the lower power levels and less sensitivity at the higher power levels.

Differential current is measured by the circuit consisting of T301, R301 and L301. As described above, when differential current flows in the primary circuit of transformer T301, the secondary produces a proportional signal indicative of the amount of differential current flow. Resistor R301 is connected across the secondary as is incandescent lamp L301 in much the same way as described above. When the differential current increases, the brilliance of lamp L301 also increases, and thus the amount of differential current can be measured by examining and quantifying the brightness of lamp L301. This is accomplished in much the same way as above by mating L301 with the CDS cell resistor R303. Thus, when differential current increases, the resistance of R303 decreases.

To detect an imbalance and trigger the alarm, CDS resistors R303 and R304 are connected in series between the power supply rails. Therefore, R303 and R304 act as a voltage divider with the output taken at the point where both components interconnect. This technique provides an offset and adjustment that will automatically compensate for the power level of the generator. For example, if the power level is set to a high current, lamp L302 will glow brightly and CDS resistor R304 will have a small resistance. This will require that the differential current measured by lamp L301 and R303 also be quite large in order for R303 to decrease to the point where the voltage will move from ground to the nominal detection range (between 2 and 7 volts). When the signal voltage is in this "detection range", the alarm function can be triggered at a level that is determined by the setting of variable resistor R307. If the power level is set to a low current, lamp L302 will glow more dimly and CDS resistor R304 will have a much higher resistance. This will require that the differential current measured by lamp L301 and R303 be much smaller to produce the same effect. The net result is that one can balance the various components utilized in this circuit to provide a trip point that is very constant, perhaps varying by only 3 to 4 centimeters of the total length of the electrode.

In order to detect and trigger the alarm, the output signal that is provided by the R303–R304 junction is smoothed by capacitors C301 and C302. Resistor R305 provides a minimum resistance for R303 to work against at very low power levels. This signal is buffered by transistor Q302 which is configured as an emitter follower and has a very high input impedance through capacitor 305. This high impedance is necessary to prevent any loading of R303–R304 which would bias the measurement signal and affect the operation of the device. Resistor R307 is the adjustable potentiometer which sets the trip point for the alarm. The wiper of R307 is connected to the anode of a LED inside integrated circuit U301. IC U301 is basically a light controlled triac which when activated causes current to flow from capacitor C304 through one of the coils of relay RL301. Resistor R307 therefore can be adjusted to provide any desired trip point location on the electrode. The relay which is an OMRON G6AK-234P latching relay, is configured via switch S301 to enable manual resetting.

Generators which employ a cable sentry detection circuit provide an A.C. or D.C. bias current that is passed through one lead of the ground return cable and sensed through the other. If the cable is interrupted, the generator will sense a fault condition. The interface module makes use of this feature in order to trip the generator fault detection circuit when a current imbalance occurs. Switch S301B is connected in series with one switch of relay RL301. When the unit is initially reset by depressing switch S301, cable sentry bias current flows up one of the ground return leads, through S301B, through RL301 and back to the generator thus completing the circuit. In addition, switch S301A, which is mechanically linked to S301B is connected to the opposite coil in relay RL301. When the trip point on the electrode is reached and current energizes the relay coil, the switch section contained in RL301 is opened causing the cable sentry to detect a fault. Depressing S301 causes the connection to be restored, while at the same time switching the trigger output to the other relay coil. This back-and-forth operation allows the unit to be reset without having to use any external power source.

Having described the present invention in detail and by reference to various embodiments thereof, it will be apparent that certain modifications and variations are possible without departing from the scope of the invention defined in the appended claims.

What is claimed is:

1. Apparatus for performing electrosurgical procedures, comprising:

an electrosurgical generator having an active electrode output connector and a return current connector, said generator providing an electrosurgical current at said active electrode output connector, said generator including a fault detection circuit for monitoring the proper operation of said generator;

an active electrode connected to said active electrode output connector for receiving said electrosurgical current from said generator and applying said electrosurgical current to a patient;

a patient return electrode, said patient return electrode providing capacitive coupling with the skin of a patient;

a patient return electrode cable, electrically connected to said patient return electrode; and an interface module electrically connected to said return current connector of said generator and to said patient return electrode cable for permitting return of said electrosurgical current from said patient to said generator via said patient return electrode and said patient return electrode cable, said interface module electrically simulating to said fault detection circuit of said electrosurgical generator a fault condition when the patient return electrode does not provide sufficient contact with the skin of a patient, whereby operation of said electrosurgical generator is terminated.

2. The apparatus for performing electrosurgical procedures of claim 1 in which said return current connector comprises a pair of connector conductors, in which said fault detection circuit for monitoring the proper operation of said generator is a return electrode monitor circuit, and in which said interface module interrupts the electrical continuity between said pair of connector conductors when the patient return electrode does not provide sufficient contact with the skin of a patient, whereby operation of said electrosurgical generator is terminated.

3. The apparatus for performing electrosurgical procedures of claim 1 in which said return current connector comprises a pair of connector conductors, in which said fault detection circuit for monitoring the proper operation of said generator is a cable continuity monitor circuit which monitors the electrical continuity between said pair of connector conductors, and in which said interface module interrupts the electrical continuity between said pair of connector conductors when the patient return electrode does not provide sufficient contact with the skin of a patient, whereby operation of said electrosurgical generator is terminated.

4. The apparatus for performing electrosurgical procedures of claim 1 in which said patient return electrode includes a pair of patient return electrode elements, each providing capacitive coupling with the skin of a patient, and in which said patient return electrode cable includes a pair of cable conductors, each cable conductor electrically connected to an associated one of said patient return electrode elements.

5. The apparatus for performing electrosurgical procedures of claim 4 in which said pair of patient return electrode elements each includes an electrically conductive layer and an overlying dielectric layer, and in which said electrically conductive layers are generally triangular in shape and not symmetrically positioned on said patient return electrode.

6. The apparatus for performing electrosurgical procedures of claim 5 in which said interface module comprises:

a toroidal coil having a center-tapped primary winding with each end of said primary winding of said toroidal coil being connected to a respective one of said pair of cable conductors, said toroidal coil and the parallel connected capacitance provided by said pair of patient return electrode elements of said patient return electrode providing a tank circuit, said toroidal coil having a secondary winding in which a current is generated that varies directly in magnitude with the degree of attachment of said patient return electrode, and the current in said tank circuit is inversely related to the degree of attachment of said patient return electrode; and a switch circuit for electrically simulating to said fault detection circuit of said electrosurgical generator a fault condition when the current in said secondary winding exceeds a predetermined level, whereby operation of said electrosurgical generator is terminated when said patient return electrode does not provide sufficient contact with the skin of a patient.

7. The apparatus for performing electrosurgical procedures of claim 6 in which said fault detection circuit for monitoring the proper operation of said generator is a cable continuity monitor circuit which monitors the electrical continuity between said pair of connector conductors, and in which said switch circuit provides an electrical connection between said pair of connector conductors when the patient return electrode provides sufficient contact with the skin of a patient and interrupts the electrical continuity between said pair of connector conductors when the patient return electrode does not provide sufficient contact with the skin of a patient, whereby operation of said electrosurgical generator is terminated.

8. The apparatus for performing electrosurgical procedures of claim 4 in which said pair of patient return electrode elements each includes an electrically conductive layer and an overlying dielectric layer, in which said patient return electrode is generally rectangular in shape, and in which said electrically conductive layers are generally triangular in shape and not symmetrically positioned with respect to a center line extending parallel to either the length or width of the patient return electrode.

9. The apparatus for performing electrosurgical procedures of claim 4 in which said interface module comprises:

a fixed frequency oscillator circuit providing an oscillating output signal;

a toroidal coil having a secondary winding connected to an output from said fixed frequency oscillator circuit, and having a center-tapped primary winding with each end of said primary winding of said toroidal coil being connected to a respective one of said pair of cable conductors, said toroidal coil and the parallel connected capacitance provided by said pair of patient return electrode elements of said patient return electrode providing a tank circuit, whereby the resonant frequency of said tank circuit varies with the degree of attachment of said patient return electrode, and the current in said tank circuit is inversely related to the degree of attachment of said patient return electrode;

a comparator circuit for comparing the current in said tank circuit to a reference level; and a switch circuit for electrically simulating to said fault detection circuit of said electrosurgical generator a fault condition when the current in said tank circuit exceeds said reference level, whereby operation of said electrosurgical generator is terminated when said patient return electrode does not provide sufficient contact with the skin of a patient.

10. The apparatus for performing electrosurgical procedures of claim 9 in which said interface module further comprises a sample and hold circuit for sampling said current in said tank circuit at the time that the patient return electrode is initially applied to a patient so as to establish said reference level, said sample and hold circuit providing said reference level to said comparator circuit.

11. The apparatus for performing electrosurgical procedures of claim 9 in which said return current connector comprises a pair of connector conductors, in which said fault detection circuit for monitoring the proper operation of said generator is a return electrode monitor circuit, and in which said interface module interrupts the electrical continuity between said pair of connector conductors when the patient return electrode does not provide sufficient contact with the skin of a patient, whereby operation of said electrosurgical generator is terminated.

12. The apparatus for performing electrosurgical procedures of claim 9 further comprising a self-test circuit for actuating the switch circuit in the event of a component failure in said interface module.

13. The apparatus for performing electrosurgical procedures of claim 9 in which said interface module further comprises a window circuit for enabling operation of said comparator circuit only during periods of time in which said generator is not supplying said electrosurgical current to said active electrode.

14. The apparatus for performing electrosurgical procedures of claim 4 in which said interface module comprises:

a variable frequency oscillator circuit providing an oscillating output signal, said oscillator circuit including a manually adjustable frequency control;

a toroidal coil having a secondary winding connected to an output from said variable frequency oscillator circuit, and having a center-tapped primary winding with each end of said primary winding of said toroidal coil being connected to a respective one of said pair of cable conductors, said toroidal coil and the parallel connected capacitance provided by said pair of patient return electrode elements of said patient return electrode providing a tank circuit, whereby the resonant frequency of said tank circuit varies with the degree of attachment of said patient return electrode, and the current in said tank circuit is inversely related to the degree of attachment of said patient return electrode;

a comparator circuit for comparing the current in said tank circuit to a reference level; and a switch circuit for electrically simulating to said fault detection circuit of said electrosurgical generator a fault condition when the current in said tank circuit exceeds said reference level, whereby operation of said electrosurgical generator is terminated when said patient return electrode does not provide sufficient contact with the skin of a patient.

15. The apparatus for performing electrosurgical procedures of claim 14 in which said return current connector comprises a pair of connector conductors, in which said fault detection circuit for monitoring the proper operation of said generator is a return electrode monitor circuit, and in which said interface module interrupts the electrical continuity between said pair of connector conductors when the patient return electrode does not provide sufficient contact with the skin of a patient, whereby operation of said electrosurgical generator is terminated.

16. The apparatus for performing electrosurgical procedures of claim 14 further comprising a self-test circuit for actuating the switch circuit in the event of a component failure in said interface module.

17. The apparatus for performing electrosurgical procedures of claim 14 in which said interface module further comprises a window circuit for enabling operation of said comparator circuit only during periods of time in which said generator is not supplying said electrosurgical current to said active electrode.

* * * * *